US009451930B2

(12) United States Patent
Abe (10) Patent No.: US 9,451,930 B2
(45) Date of Patent: Sep. 27, 2016

(54) ULTRASONIC DIAGNOSIS APPARATUS, ULTRASONIC IMAGE PROCESSING APPARATUS, AND RECORDING MEDIUM ON WHICH ULTRASONIC IMAGE PROCESSING PROGRAM IS RECORDED

(75) Inventor: Yasuhiko Abe, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 790 days.

(21) Appl. No.: 12/606,249

(22) Filed: Oct. 27, 2009

(65) Prior Publication Data

US 2010/0041994 A1   Feb. 18, 2010

(30) Foreign Application Priority Data

Feb. 25, 2008   (JP) ................. 2008-043142

(51) Int. Cl.
*A61B 8/14*   (2006.01)
*A61B 8/00*   (2006.01)
*G01S 7/52*   (2006.01)
(Continued)

(52) U.S. Cl.
CPC .............. *A61B 8/429* (2013.01); *A61B 8/463* (2013.01); *A61B 8/485* (2013.01); *A61B 8/488* (2013.01); *G01S 7/52042* (2013.01); *G01S 15/8979* (2013.01); *A61B 5/7242* (2013.01); *A61B 8/08* (2013.01); *A61B 8/0883* (2013.01); *A61B 8/4245* (2013.01)

(58) Field of Classification Search
CPC ........................ A61B 5/7242; A61B 8/0883
USPC .......... 73/597; 600/437, 438, 440, 441, 443, 600/447, 455, 459, 587
See application file for complete search history.

(56) References Cited

U.S. PATENT DOCUMENTS 5,178,147 A * 1/1993 Ophir et al. ................. 600/437
5,293,870 A * 3/1994 Ophir et al. ................. 600/437
(Continued)

FOREIGN PATENT DOCUMENTS

EP   1 652 477 A1   5/2006
EP   1 804 078 A1   7/2007
(Continued)

OTHER PUBLICATIONS

English Translation of JP20040155630, May 26, 2004.*
(Continued)

*Primary Examiner* — Serkan Akar
(74) *Attorney, Agent, or Firm* — Oblon, McClelland, Maier & Neustadt, L.L.P.

(57) ABSTRACT

The average velocity of a tissue is calculated for each frame in accordance with compression/release, and a reference waveform is generated by using the calculated velocity. A time phase in which the average velocity becomes 0 is specified by the reference waveform. In strain computation, time integration is performed for strain computation in a compression period or a release period with reference to the specified stationary time phase. This can properly and automatically visualize how the contraction of the tissue is accumulated from the start of compression or the contraction of the tissue becomes maximum in a compression end time phase in a compression period and how the tissue expands from the start of release or the expansion of the tissue becomes maximum in a release end time phase in a release time phase.

17 Claims, 8 Drawing Sheets

(51) Int. Cl.
*G01S 15/89* (2006.01)
*A61B 8/08* (2006.01)
*A61B 5/00* (2006.01)

(56) References Cited

U.S. PATENT DOCUMENTS

| | | | |
|---|---|---|---|
| 5,474,070 A * | 12/1995 | Ophir et al. | 600/437 |
| 5,804,727 A * | 9/1998 | Lu et al. | 73/597 |
| 5,836,894 A * | 11/1998 | Sarvazyan | 600/587 |
| 6,099,471 A * | 8/2000 | Torp et al. | 600/438 |
| 6,113,543 A * | 9/2000 | Bonnefous | 600/438 |
| 6,352,507 B1 * | 3/2002 | Torp et al. | 600/438 |
| 7,892,188 B2 * | 2/2011 | Walker et al. | 600/587 |
| 7,938,778 B2 * | 5/2011 | Sakai | 600/437 |
| 2003/0083578 A1 * | 5/2003 | Abe et al. | 600/447 |
| 2004/0111028 A1 * | 6/2004 | Abe et al. | 600/437 |
| 2006/0036172 A1 * | 2/2006 | Abe | 600/443 |
| 2006/0052696 A1 * | 3/2006 | Shiina et al. | 600/437 |
| 2006/0122512 A1 * | 6/2006 | Abe | 600/454 |
| 2006/0244744 A1 * | 11/2006 | Kandori et al. | 345/418 |
| 2007/0112270 A1 * | 5/2007 | Waki et al. | 600/455 |
| 2007/0167777 A1 * | 7/2007 | Abe et al. | 600/441 |
| 2007/0191901 A1 * | 8/2007 | Schecter | 607/17 |
| 2007/0244390 A1 * | 10/2007 | Matsumura | 600/437 |
| 2008/0021318 A1 * | 1/2008 | Kato et al. | 600/437 |
| 2008/0086055 A1 * | 4/2008 | Sakai et al. | 600/438 |
| 2008/0269606 A1 * | 10/2008 | Matsumura | 600/438 |
| 2009/0030324 A1 * | 1/2009 | Kato et al. | 600/459 |
| 2009/0043196 A1 * | 2/2009 | Sakai et al. | 600/437 |
| 2009/0069680 A1 * | 3/2009 | Abe | 600/440 |
| 2009/0105589 A1 * | 4/2009 | Osaka et al. | 600/443 |
| 2009/0124903 A1 * | 5/2009 | Osaka | 600/443 |
| 2009/0171200 A1 * | 7/2009 | Sakai | 600/438 |
| 2010/0016721 A1 * | 1/2010 | Kanai et al. | 600/443 |
| 2010/0016724 A1 * | 1/2010 | Arai et al. | 600/443 |
| 2010/0041994 A1 * | 2/2010 | Abe | 600/443 |
| 2010/0081935 A1 * | 4/2010 | Matsumura et al. | 600/443 |
| 2010/0331691 A1 * | 12/2010 | Okamura et al. | 600/443 |

FOREIGN PATENT DOCUMENTS

| | | | |
|---|---|---|---|
| JP | 2003-175041 | 6/2003 | |
| JP | 2004-351062 | 12/2004 | |
| JP | 2005-270341 | 10/2005 | |
| JP | 2005-334196 | 12/2005 | |
| JP | 2007-282932 | 11/2007 | |
| JP | 2008-237664 | 10/2008 | |
| WO | WO 2005/120358 A1 | 12/2005 | |
| WO | WO 2005/122907 A1 | 12/2005 | |
| WO | WO 2006/132203 * | 12/2006 | A61B 8/08 |

OTHER PUBLICATIONS

European Search Report issued Jan. 20, 2012, in Patent Application No. 09715919.8.

* cited by examiner

ULTRASONIC DIAGNOSIS APPARATUS, ULTRASONIC IMAGE PROCESSING APPARATUS, AND RECORDING MEDIUM ON WHICH ULTRASONIC IMAGE PROCESSING PROGRAM IS RECORDED

CROSS-REFERENCE TO RELATED APPLICATIONS

This is a Continuation application of PCT Application No. PCT/JP2009/053428, filed Feb. 25, 2009, which was published under PCT Article 21(2) in Japanese.

This application is based upon and claims the benefit of priority from prior Japanese Patent Application No. 2008-043142, filed Feb. 25, 2008, the entire contents of which are incorporated herein by reference.

BACKGROUND OF THE INVENTION

1. Field of the Invention

The present invention relates to a technique in a case in which tissue strain imaging (TSI) is applied to elastic imaging to estimate a local hardness distribution from the strain state of a biological soft tissue.

2. Description of the Related Art

In ultrasonic diagnosis, the pulsation of the heart or the movement of a fetus can be displayed in real time by the simple operation of bringing an ultrasonic probe into contact with the surface of the body. In addition, this technique is highly safety, and hence allows repetitive examination. Furthermore, the size of this system is smaller than those of other diagnosis apparatuses such as X-ray, CT, and MRI apparatuses, and hence can be said to be a simple diagnosis technique which facilitates examination to be performed by moving the apparatus to the bed side. Ultrasonic diagnosis apparatuses used in this ultrasonic diagnosis vary in type depending on the functions which they have. Some compact apparatuses which have already been developed are small enough to be carried with one hand. Ultrasonic diagnosis is free from the influence of radiation exposure such as X-ray exposure, and hence can be used in obstetric treatment, treatment at home, and the like.

It is very important for tissue diagnosis to objectively and quantitatively evaluate the function of a living tissue such as cardiac muscle by using such an ultrasonic diagnosis apparatus. For example, there has recently been commercialized, as a quantitative evaluation method for the heart, a technique of calculating local myocardial wall motion information such as displacement or strain while performing local pattern matching in images (see, for example, Jpn. Pat. Appln. KOKAI Publication No. 2003-175041). There is available a technique of accurately computing the three-dimensional distribution of myocardial wall motion information by using an ultrasonic diagnosis apparatus capable of acquiring three-dimensional images (see Jpn. Pat. Appln. KOKAI Publication No. 2003-175041). These techniques allow to acquire three-dimensional myocardial wall motion information and the like and quantitatively evaluate the function of a tissue.

As an image diagnosis technique using an ultrasonic diagnosis apparatus, a technique called elastic imaging is available. This technique applies a dynamic load to a tissue to compress/expand it, and measures a motion (dynamic response) in response to the application of the load, thereby acquiring and visualizing elastic information. Recently, there has been developed a technique of determining and displaying the current pressed state (pressing strength) by using displacement information obtained from between two frames when performing this elastic imaging (i.e., a technique which applies TSI to elastic imaging) (see, for example, Jpn. Pat. Appln. KOKAI Publication No. 2004-351062).

BRIEF SUMMARY OF THE INVENTION

When TSI is applied to elastic imaging by using a conventional ultrasonic diagnosis apparatus, for example, the following problems arise.

First of all, when elastic imaging based on TSI is to be performed for a soft tissue such as mammary glands, the deformation of the soft tissue is induced by, for example, repeating compression and release using a probe. In this case, since there is no guarantee that a time phase suitable for the start of strain computation is synchronous with deformation motion, an optimal strain image which produces the maximum strain relative to the strain before deformation cannot sometimes be obtained after deformation.

In addition, when the compression and release are performed by using the probe, it is not possible to recognize the time phase of deformation (for example, the extent to which the tissue is currently compressed or released).

These problems arise from the fact that there is no proper reference (synchronization) signal in the case of induction of deformation, in which compression and release are repeated by the probe, unlike the case of the heart in which a biological signal such as an ECG signal is synchronous with the motion of a target tissue and hence serves as a reference signal.

The present invention has been made in consideration of the above situation, and has as its object to provide an ultrasonic diagnosis apparatus, an ultrasonic image processing apparatus, and a recording medium on which an ultrasonic image processing program is recorded, which can generate and display reference information serving as a suitable reference in a case in which a time phase suitable for the start of strain computation is determined and a dynamic load is applied to a tissue in elastic imaging using TSI.

According to a first aspect of the present invention, an ultrasonic diagnosis apparatus comprising: an image data acquisition unit which acquires ultrasonic image data corresponding to each time phase in a first period including at least one contraction and one expansion by ultrasonic scanning throughout the first period for an observation region of an object to be examined which repeats contracting motion and expanding motion upon application of a dynamic load including repetition of compression and release; a velocity information generating unit which generates velocity information concerning a tissue in the observation region in each time phase in the first period; a reference information generating unit which generates reference information indicating a change in the contracting motion and the expanding motion with time; a strain information generating unit which generates strain information concerning the tissue in the observation region based on the reference information and velocity information in said each time phase; an image generating unit which generates, based on strain information, a strain image indicating a strain distribution of the observation region; and a display unit which displays the strain image in a predetermined form.

According to a second aspect of the present invention, an ultrasonic image processing apparatus comprising: a storage unit which stores ultrasonic image data corresponding to each time phase in a first period including at least one contraction and one expansion by ultrasonic scanning throughout the first period for an observation region of an object to be examined which repeats contracting motion and expanding motion upon application of a dynamic load including repetition of compression and release; a velocity information generating unit which generates velocity information concerning a tissue in the observation region in each time phase in the first period; a reference information generating unit which generates reference information indicating a change in the contracting motion and the expanding motion with time; a strain information generating unit which generates strain information concerning the tissue in the observation region based on the reference information and velocity information in said each time phase; an image generating unit which generates, based on strain information, a strain image indicating a strain distribution of the observation region; and a display unit which displays the strain image in a predetermined form.

According to a third aspect of the present invention, a recording medium which records an ultrasonic image processing program which causes a computer to execute a velocity information generating function of generating velocity information concerning a tissue in an observation region in each time phase in a first period including at least one contraction and one expansion by using ultrasonic image data corresponding to each time phase in the first period by ultrasonic scanning throughout the first period for the observation region of an object to be examined which repeats contracting motion and expanding motion upon application of a dynamic load including repetition of compression and release, a reference information generation function of generating reference information indicating a change in the contracting motion and the expanding motion with time, a strain information generating function of generating strain information concerning the tissue in the observation region based on the reference information and velocity information in said each time phase, and an image generating function of generating, based on strain information, a strain image indicating a strain distribution of the observation region.

DETAILED DESCRIPTION OF THE INVENTION

The first to fourth embodiments of the present invention will be described with reference to the accompanying drawings. Note that throughout the drawings, the same reference numerals denote constituent elements having same or similar functions, and a repetitive description thereof will be avoided.

(First Embodiment)

Figure 1:
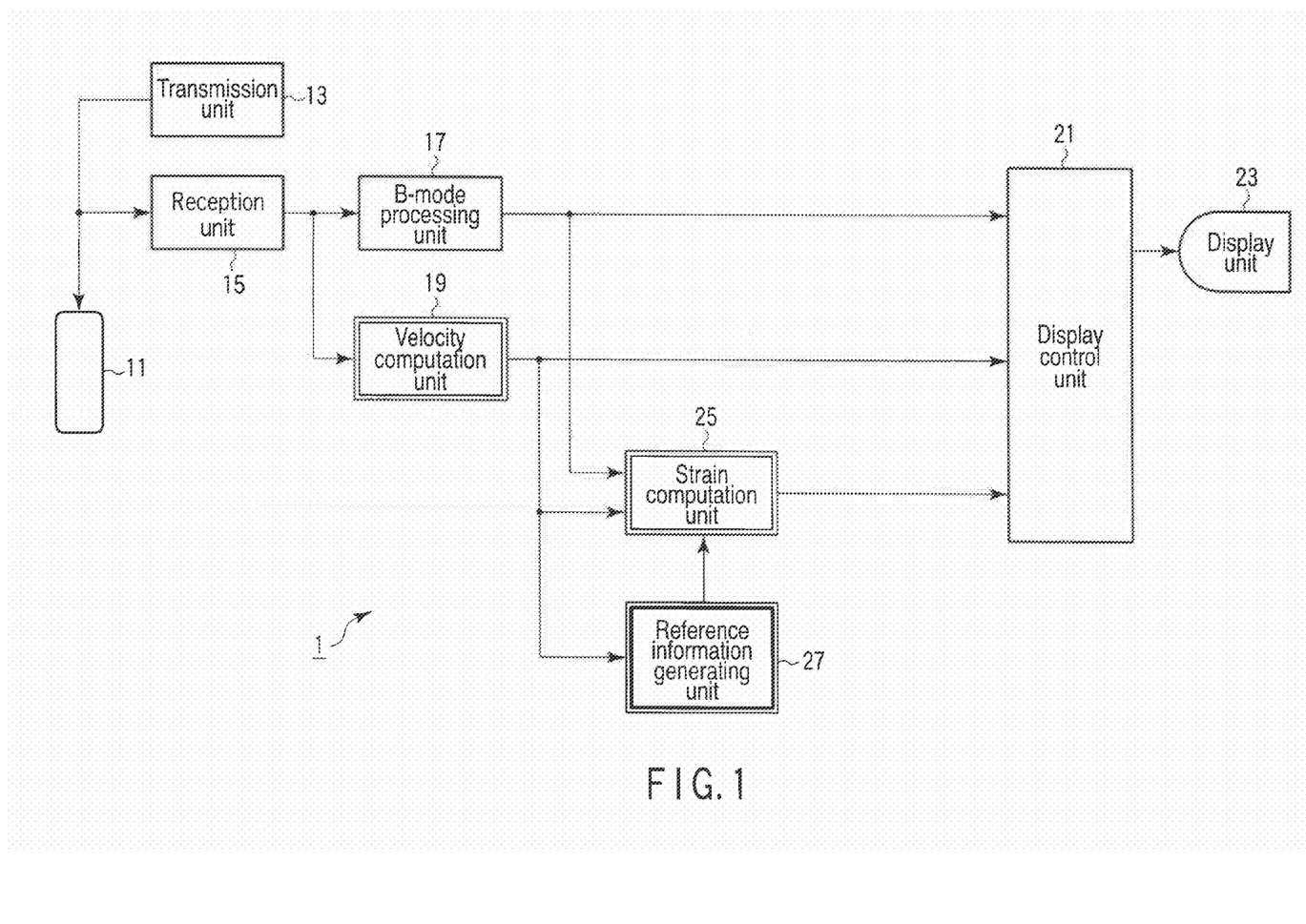
FIG. 1 is a block diagram for explaining the arrangement of an ultrasonic diagnosis apparatus according to the first embodiment.

FIG. 1 is a block diagram showing the arrangement of an ultrasonic diagnosis apparatus 1 according to this embodiment. An ultrasonic diagnosis apparatus includes an ultrasonic probe 11, a transmission unit 13, a reception unit 15, a B-mode processing unit 17, a velocity computation unit 19, a display control unit 21, a display unit 23, a strain computation unit 25, and a reference information generating unit 27.

The ultrasonic probe 11 generates ultrasonic waves based on a driving signal from the transmission unit 13, and includes a plurality of piezoelectric vibrators which convert reflected waves from an object to be examined into electrical signals, a matching layer provided for the piezoelectric vibrators, and a backing member which prevents ultrasonic waves from propagating backward from the piezoelectric vibrators. When ultrasonic waves are transmitted from the ultrasonic probe 11 to the object, various harmonic components are generated due to the nonlinearity of a living tissue upon propagation of ultrasonic waves. Fundamental waves and harmonic components constituting transmission ultrasonic waves are scattered backward by acoustic impedance boundaries of a tissue in the living body, micro-scattering, and the like, and are received as reflected waves (echoes) by the ultrasonic probe 11.

The transmission unit 13 includes a delay circuit and pulser circuit (not shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The transmission unit 13 applies a driving pulse to each vibrator so as to form an ultrasonic beam toward a predetermined scan line at the timing based on this rate pulse.

The reception unit 15 includes an amplifier circuit, A/D converter, and adder which are not shown. The amplifier circuit amplifies an echo signal received through the probe 11 for each channel. The A/D converter gives the amplified echo signals delay times necessary to determine reception directivities. The adder then performs addition processing for the signals. With this addition, an ultrasonic echo signal corresponding to a predetermined scan line is generated.

The B-mode processing unit 17 performs envelope detection processing for the ultrasonic echo signal received from the reception unit 15 to generate a B-mode signal corresponding to the amplitude intensity of the ultrasonic echo.

The velocity computation unit 19 performs quadrature detection processing, autocorrelation processing, and delay/addition processing for the echo signal acquired by tissue Doppler imaging, and obtains, based on the Doppler shift component of the echo signal having undergone delay/addition processing, a tissue Doppler signal corresponding to the velocity, variance, and power of the tissue which moves in the object. The velocity computation unit 19 generates, for each time phase in a predetermined period, a tissue Doppler image representing the two-dimensional distribution of velocities, variances, and power values which is associated with a predetermined slice by using the tissue Doppler signal. Note that the predetermined period is an arbitrary period including repetitive compression/release with respect to a diagnosis target. The velocity computation unit 19 also generates a spatiotemporal distribution image (an image representing the velocity of the diagnosis target tissue at each position, which will be referred to as velocity distribution information hereinafter) of tissue velocities in the respective time phases in the predetermined period by using a tissue Doppler image in each time phase in the predetermined period.

The display control unit 21 generates an ultrasonic diagnosis image (a B-mode ultrasonic image, strain image, or the like) or reference waveform as a display image by converting (scan-converting) the scanning line signal string for ultrasonic scanning into a scanning line signal string in a general video format typified by a TV format.

The display unit 23 displays a B-mode ultrasonic image, strain image, and reference waveform in predetermined forms and at predetermined timings based on video signals from the display control unit 21. The display unit 23 also displays a marker indicating anatomical position on an image and a color bar indicating the magnitude of a color-coded physical quantity.

The strain computation unit 25 obtains a displacement by time-integrating predetermined motion direction components of velocity associated with a region of interest by using each reference time phase (to be described later) determined by using velocity distribution information and reference information associated with each time phase in a predetermined period. The strain computation unit 25 computes the local strain of the tissue for each time phase by performing predetermined computation using the obtained displacement. The strain computation unit 25 generates a strain image by converting the obtained local strain of the tissue for each time phase into a color code and mapping it at a corresponding position.

The reference information generating unit 27 computes the average tissue velocity for each frame by using the velocity distribution information associated with each time phase in the predetermined period. In addition, the reference information generating unit 27 generates a reference waveform by plotting the average tissue velocity for each frame in time series.

(Reference Information Generation/Display Function)

The reference information generation/display function of the ultrasonic diagnosis apparatus 1 will be described next. In elastic imaging using TSI, this function serves to generate reference information as a proper reference and display it in a predetermined form when a time phase suitable for the start of strain computation is determined or a dynamic load is applied to the tissue. Assume that in this embodiment, for a concrete description, a waveform (reference waveform) indicating a temporal change in the average tissue velocity for each frame is generated as reference information.

Figure 2:
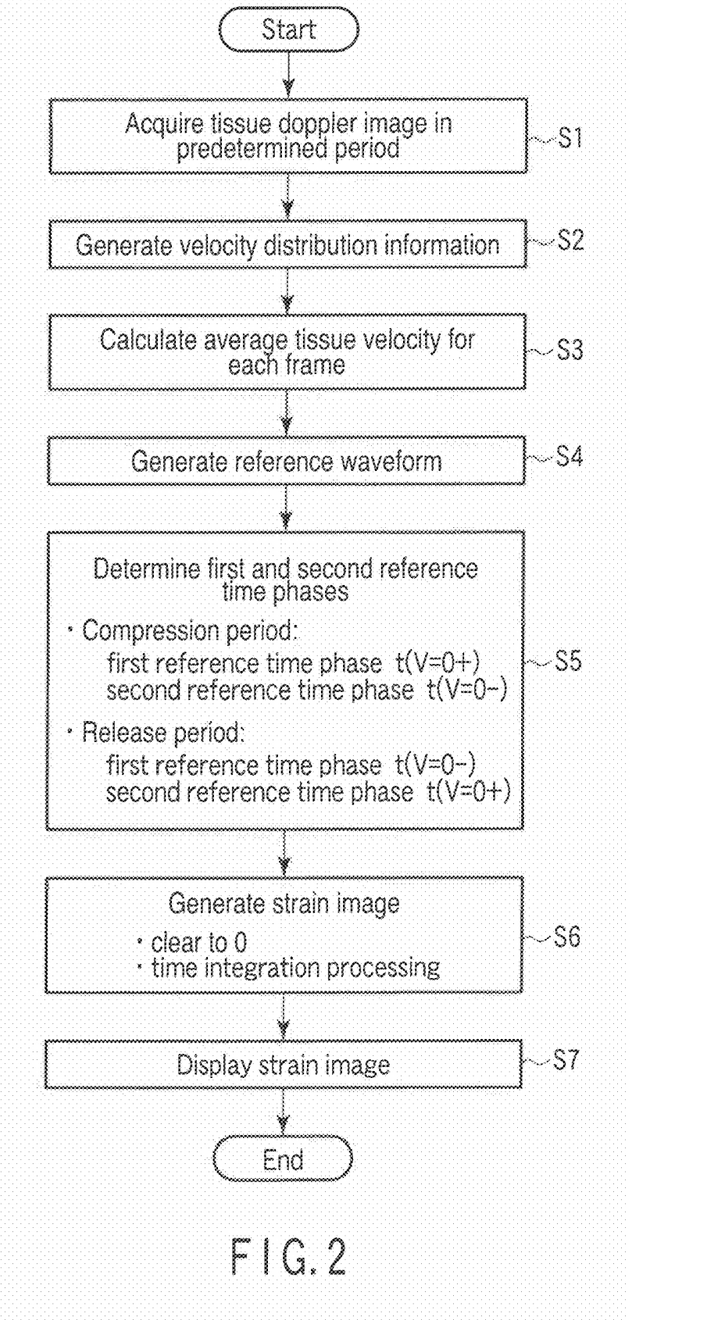
FIG. 2 is a flowchart showing a processing sequence in the execution of elastic imaging using TSI with the use of a reference information generation/display function.

FIG. 2 is a flowchart showing a processing sequence in the execution of elastic imaging using TSI with the use of the reference information generation/display function. This sequence will be described below with reference to FIG. 2.

[Acquisition of Tissue Doppler Image in Each Time Phase in Predetermined Period: Step S1]

First of all, a tissue Doppler image is acquired in each time phase in a predetermined period for a desired observation region of a soft tissue (e.g., a breast) of a given object by the tissue Doppler method (step S1).

[Generation of Velocity Distribution Information in Each Time Phase in Predetermined Period: Step S2]

The velocity computation unit 19 then generates velocity distribution information in each time phase in the predetermined period by using the tissue Doppler image associated with each time phase in the predetermined period and the motion field set by a predetermined technique (step S2). As a technique of generating this velocity distribution information, for example, the technique disclosed in Jpn. Pat. Appln. KOKAI Publication No. 2003-175041 can be used.

[Calculation of Average Tissue Velocity for Each Frame: Step S3]

The reference information generating unit 27 then calculates an average tissue velocity for each frame by using velocity distribution information in each time phase in the predetermined period (step S3). In this case, in a period during which the observation region is compressed by the ultrasonic probe 11, the observation region and the ultrasonic probe 11 relatively come close to each other. The moving direction of the tissue (i.e., the direction of velocity) in this period is defined as positive. On the other hand, in a period during which the ultrasonic probe 11 stops compressing (i.e., releases) the observation region, the observation region and the ultrasonic probe 11 relatively separate from each other. The moving direction of the tissue (i.e., the direction of velocity) in this period is defined as negative.

[Generation of Reference Waveform: Step S4]

The reference information generating unit 27 then plots the average tissue velocity for each frame in the predetermined period in time series, and performs predetermined interpolation processing as needed, thereby generating a reference waveform indicating a change in average tissue velocity with time (step S4).

Figure 3:
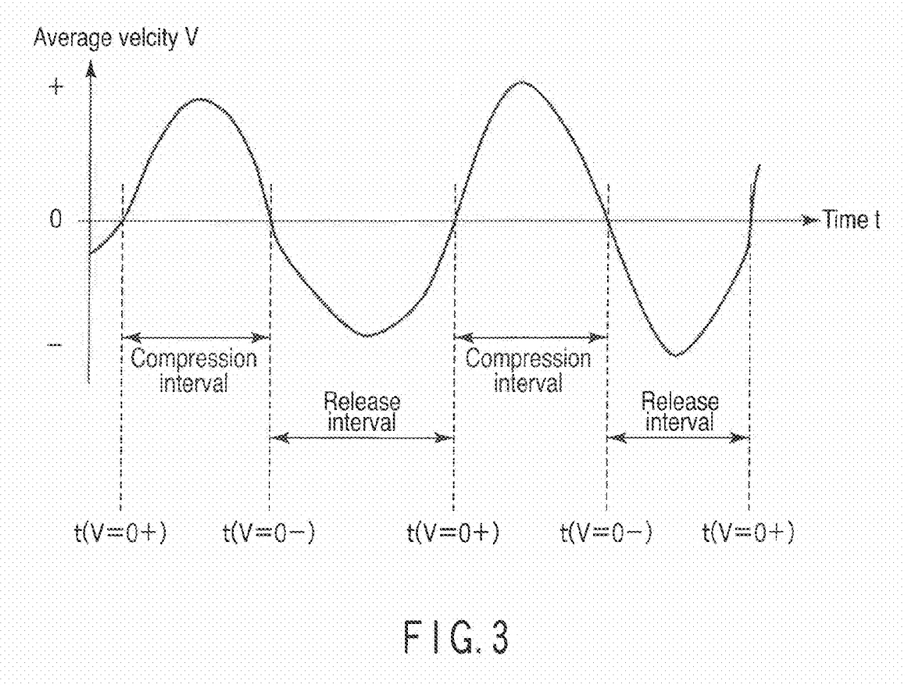
FIG. 3 is a graph showing an example of the reference waveform generated in step S4 in the flowchart shown in FIG. 2.

FIG. 3 is a graph showing an example of the reference waveform generated in step S4. As shown in FIG. 3, when the observation region is repeatedly compressed and released by the ultrasonic probe 11, the average tissue velocity periodically changes positively and negatively. Note that the expression "V=0+" in this graph indicates a time point corresponding to velocity V=0 in the process of a change in average tissue velocity from a negative value to a positive value (i.e., the process of a change from a released state to a compressed state), and the expression "V=0−" indicates a time point corresponding to velocity V=0 in the process of a change in average tissue velocity from a positive value to a negative value (i.e., the process of a change from a compressed state to a released state). Therefore, on the reference waveform, the period from time t(V=0+) corresponding to V=0+ to time t(V=0−) corresponding to V=0− corresponds to a compression period, and the period from time t(V=0−) corresponding to V=0− to time t(V=0+) corresponding to V=0+ corresponds to a release period.

[Determination of Reference Time Phase: Step S5]

The strain computation unit 25 then determines the first and second reference time phases used in strain computation based on the reference waveform (step S5). In this case, the first reference time phase is a time phase corresponding to the lower limit of the integral interval of time integration executed in strain computation. The second reference time phase is a time phase corresponding to the end of the updating of the upper limit of the integral interval in the time integration in strain computation.

That is, when generating a strain image in each compression period, the strain computation unit 25 determines, based on the reference waveform, time t(V=0+) corresponding to V=0+ in each compression period as the first reference time phase, and time t(V=0−) corresponding to V=0− in each compression period as the second reference time phase.

When generating a strain image in each release period, the strain computation unit 25 determines, based on the reference waveform, time $t(V=0-)$ corresponding to $V=0-$ in each compression period as the first reference time phase, and time $t(V=0+)$ corresponding to $V=0+$ in each compression period as the second reference time phase.

[Step S6: Generation of Strain Image]

The strain computation unit 25 then obtains a displacement by time-integrating predetermined motion direction components of velocity associated with a region of interest by using the determined first and second reference time phases, and computes the local strain of the tissue by performing predetermined computation using the obtained displacement. That is, the strain computation unit 25 sets the lower limit of an integral interval in a compression period or a release period as the first reference time phase, and resets a strain value. The strain computation unit 25 then calculates a strain associated with the region of interest for each time phase by accumulatively executing time integration while sequentially updating the upper limit of an integral interval to a new time phase. In this calculation, when the updated time phase becomes the second reference time phase, the strain computation unit 25 performs time integration with the second reference time phase being the upper limit of an integral interval. A series of these processes is repeatedly executed as needed every time an interval is updated. In this case, the strain computation unit 25 computes the local strain of the tissue for each time phase by performing predetermined computation using the displacement obtained for each time phase, and generates a strain image for each time phase by color-coding and mapping each strain at a corresponding position (step S6).

A preferable form of use of the ultrasonic diagnosis apparatus 1, from the point of view of convenience of observation, is that it is determined in advance whether to generate a strain image in one of a compression period and a release period. If, for example, it is determined that a strain image is generated in a compression period, the processing in the steps is repeatedly executed for each compression period.

[Step S7: Display of Strain Image]

The display control unit 21 then controls the display unit 23 to display the generated strain image in a predetermined form (step S7).

Figure 4:
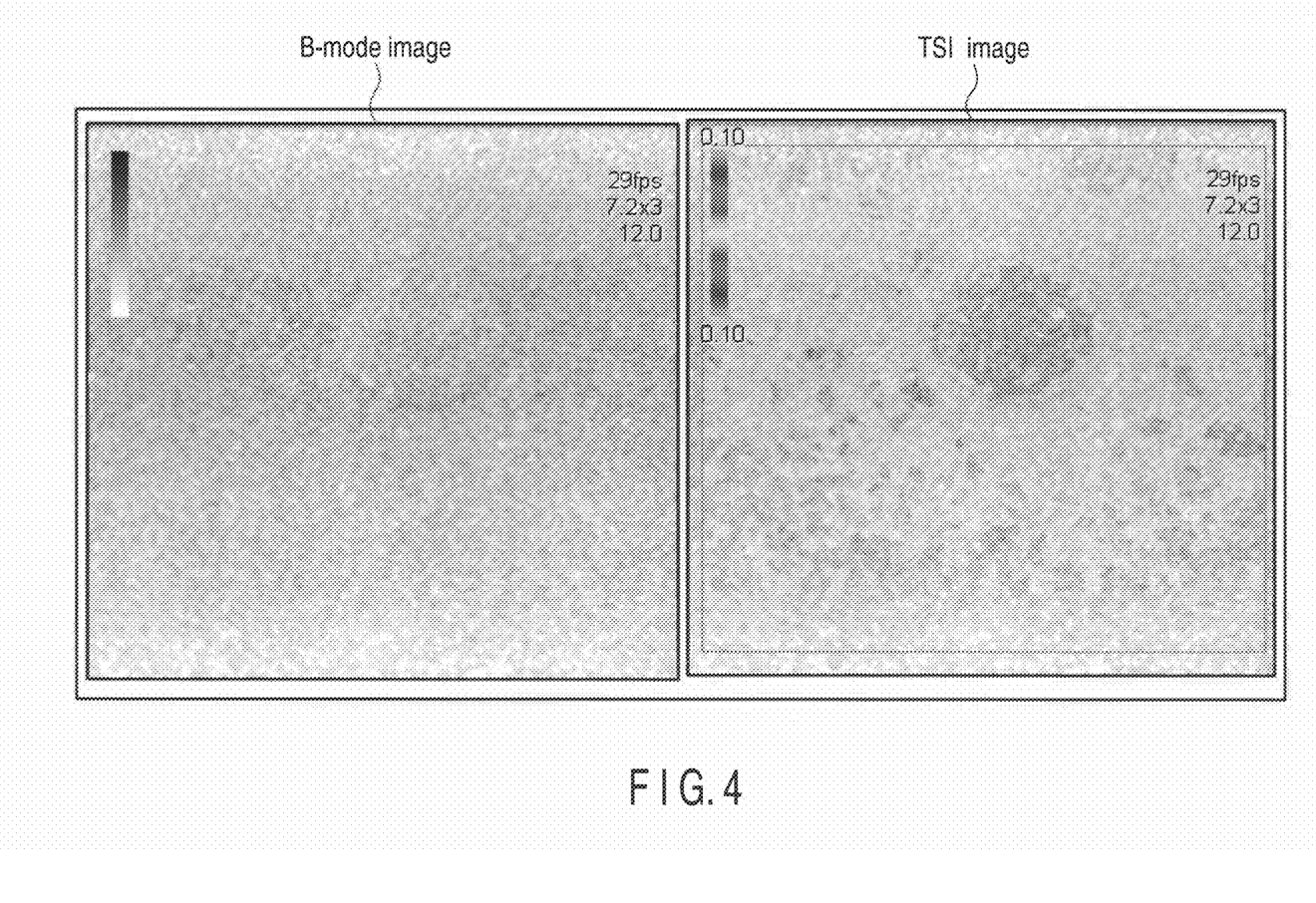
FIG. 4 is a view showing an example of a suitable display form of a strain image.

FIG. 4 shows an example of a preferred display form of a strain image. In this form, a B-mode image and a strain image are displayed side by side. In this case, the B-mode image is sequentially updated with an image in a new time phase and dynamically displayed. On the other hand, the strain image is dynamically displayed in synchronism with the B-mode image in each compression period, while the strain image (i.e., the image generated by using time integration with the lower and upper limits of an integral interval being the first and second time phases, respectively) corresponding to last time phase $t(V=0+)$ in the compression period is held/displayed until the next compression period (i.e., during a release period). According to this display form, even in a time phase in which a TSI image is held, the operator can always grasp the contact state of the probe or the state of a slice by using a B-mode image.

For example, in each compression period, the displacement amount (contraction amount) of the tissue cumulatively increases from start time $t(V=0-)$ of compression, and becomes maximum at end time $t(V=0+)$. Therefore, holding and displaying a strain image corresponding to the last time phase $t(V=0+)$ in each compression period up to the next compression period allows to observe the stain image having the maximum strain difference concerning the contraction of the tissue.

The display control unit 21 also displays the reference waveform on the display unit 23 in real time, together with the B-mode image and the strain image. At this time, the reference waveform is preferably displayed in a form similar to that of, for example, a pulse Doppler waveform or ECG waveform, while indicating to which time phase on the waveform the B-mode image and strain image correspond. In addition, when the reference waveform is to be displayed, it is preferable to set the display scale in accordance with, for example, a compression strength.

(Effects)

According to the above arrangement, the following effects can be achieved.

This ultrasonic diagnosis apparatus calculates the average velocity of the tissue corresponding to compression/release for each frame, and generates a reference waveform by using each average velocity. The apparatus specifies a time phase corresponding to an average velocity of 0 (i.e., a stationary time phase of the tissue) by using this reference waveform. In strain computation, the apparatus then performs time integration for the strain computation in a compression period or a release period with reference to the specified stationary time phase. It is therefore possible to properly and automatically visualize how the contraction of the tissue is accumulated from the start of compression (i.e., a time phase corresponding to $V=0+$) or the contraction of the tissue in a compression end time phase (i.e., a time phase corresponding to $V=0+$) becomes maximum in a compression period, or how the tissue expands from the start of release (i.e., a time phase corresponding to $V=0-$) or the expansion of the tissue in a release end time phase (i.e., a time phase corresponding to $V=0+$) becomes maximum in a release time phase. The observer can perform image diagnosis with higher quality by observing strain images in which these states are visualized.

This ultrasonic diagnosis apparatus displays the generated reference waveform in synchronism with an ultrasonic image displayed in real time as in the case of a pulse Doppler waveform, ECG waveform, or the like. This allows the probe operator to easily grasp the whereabout of the current time phase in a compression period or release period by observing a displayed reference waveform. In addition, when a strain image is held and displayed (freeze-displayed), the operator can easily grasp the whereabout of the current time phase of the strain image in a compression period or release period by referring to the position of a time phase corresponding to the image held and displayed on the reference waveform.

This ultrasonic diagnosis apparatus sets a display scale in accordance with a compression strength when displaying a reference waveform. The probe operator can monitor a compression strength by referring to the reference waveform displayed in this manner. For example, when a waveform is saturated and discontinuously displayed, the operator can monitor that the compression strength is large. When a waveform is displayed with an amplitude which is too small relative to a display scale, the operator can monitor that the compression strength is small.

(Second Embodiment)

The second embodiment of the present invention will be described next. An ultrasonic diagnosis apparatus according to this embodiment obtains a region of interest which is a characteristic region (e.g., a region with the highest luminance or a spatial edge region whose spatial differential coefficient value is high) from a B-mode image up to a predetermined period, and obtains the moving vector information and moving velocity information of the tissue by pattern matching processing between two frames.

Figure 5:
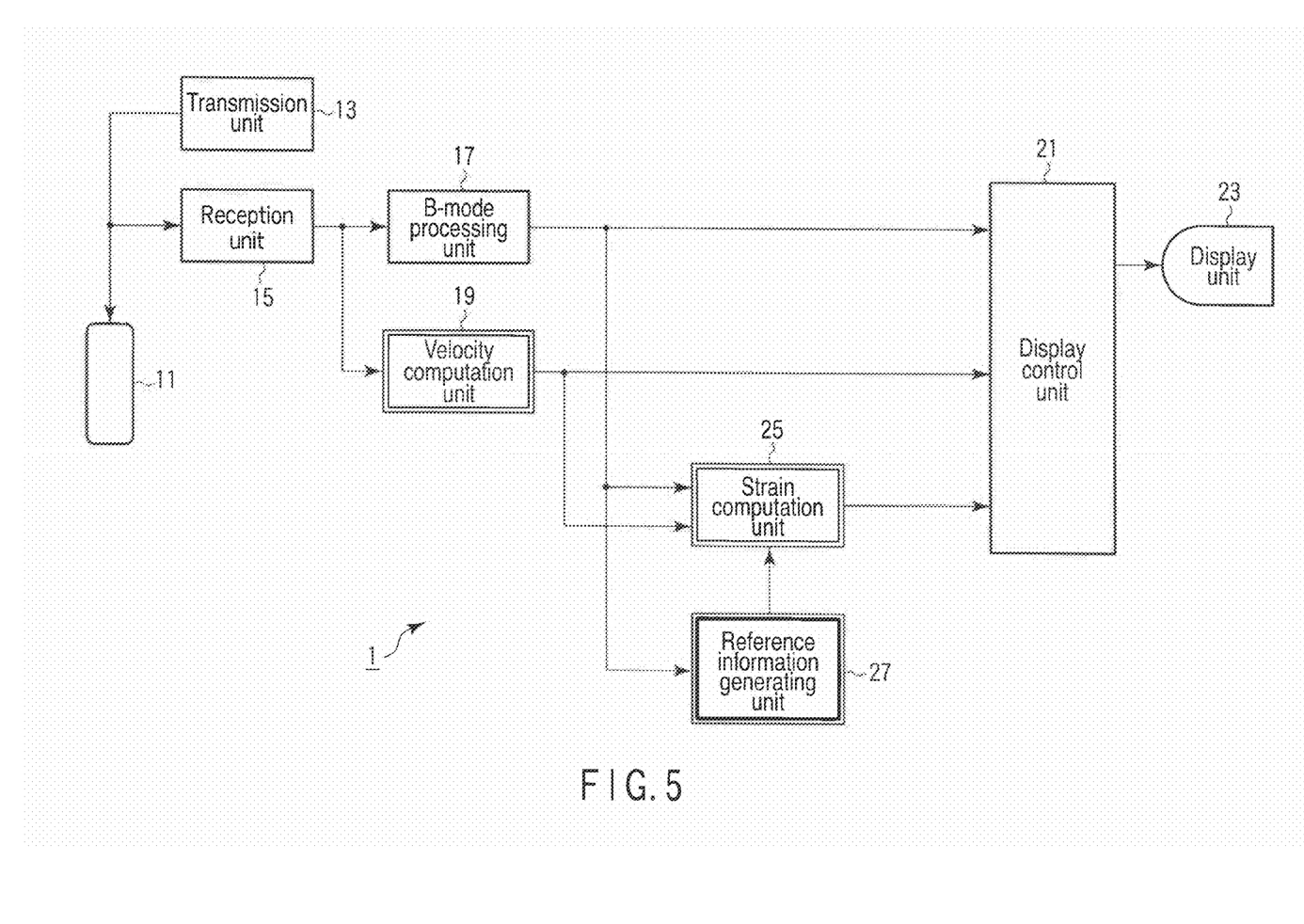
FIG. 5 is a block diagram for explaining the arrangement of an ultrasonic diagnosis apparatus 1 according to the second embodiment.

FIG. 5 is a block diagram for explaining the arrangement of the ultrasonic diagnosis apparatus according to the second embodiment. In comparison with the arrangement shown in FIG. 1, the arrangement in FIG. 5 mainly differs in the function of a strain computation unit 25.

That is, the strain computation unit 25 detects the moving position of the tissue by using pattern matching processing between two two-dimensional image data in different time phases or two volume data in different time phases, and obtains the moving vector (or the velocity) of each tissue based on the moving position. More specifically, the strain computation unit 25 can obtain the moving vector of the tissue by obtaining, with regard to a region of interest in one two-dimensional image data, a region of interest in the other two-dimensional image data which has the highest similarity and obtaining the distance between the regions of interest. The strain computation unit 25 can also obtain the moving velocity of the tissue by dividing the magnitude of this moving vector (i.e., the moving amount) by the time difference between the frames of the two-dimensional image data. Performing this processing at each position on two-dimensional image data frame by frame can acquire spatiotemporal distribution data (moving vector information) associated with the displacement (moving vector) of the tissue or the velocity of the tissue.

Figure 6:
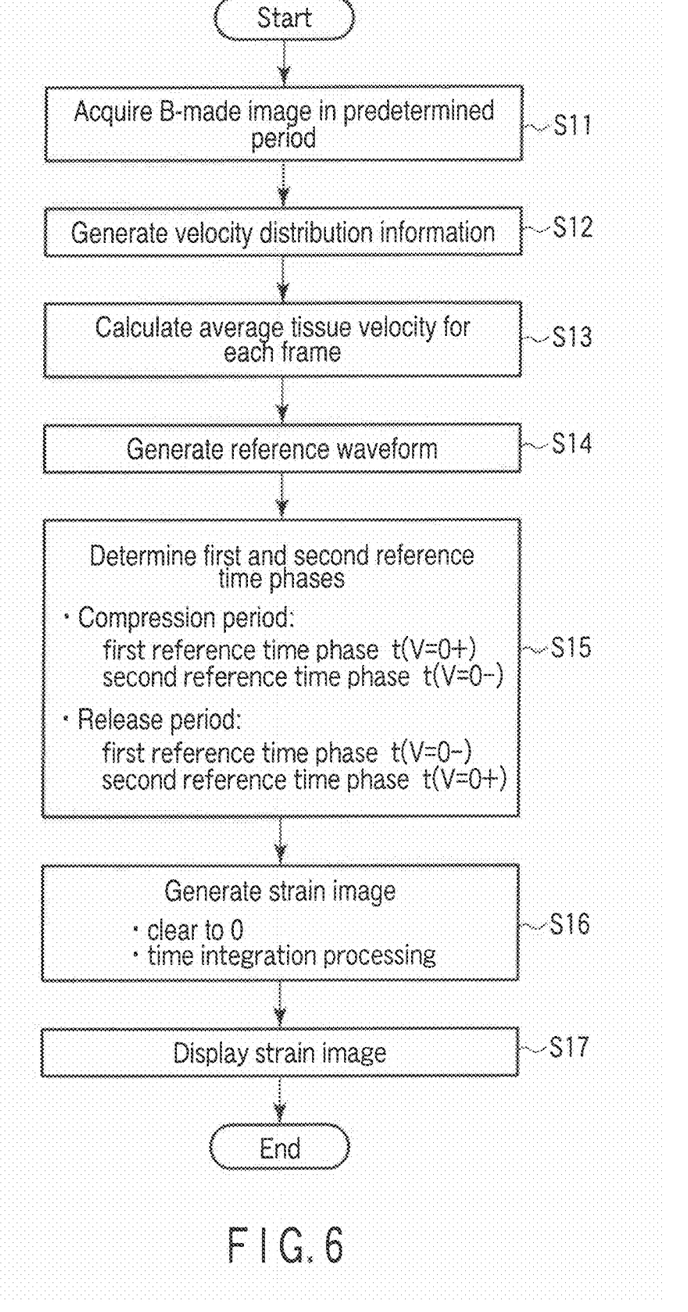
FIG. 6 is a flowchart showing a processing sequence in the execution of elastic imaging using TSI according to the second embodiment.

FIG. 6 is a flowchart showing a processing sequence in the execution of elastic imaging using TSI according to the second embodiment. This flowchart differs from that of FIG. 2 in steps S11 and S12. Processing in these steps will be described below.

[Acquisition of B-Mode Image in Each Time Phase in Predetermined Period Step S11]

First of all, an ultrasonic image in each time phase in a predetermined period is acquired from a desired observation region of a soft tissue (e.g., mammary glands) of an object by the B-mode imaging method (step S11).

[Generation of Velocity Distribution Information in Each Time Phase in Predetermined Period: Step S12]

Each tissue motion information is then generated (step S12). That is, the strain computation unit 25 extracts a region of interest of a myocardial region, based on an instruction or the like from the user, from two-dimensional image data which constitute an acquired time-series two-dimensional image data group. The strain computation unit 25 then computes spatiotemporal moving vector information by temporally tracking the extracted region of interest by two-dimensional pattern matching processing. In addition, the strain computation unit 25 obtains tissue distribution information indicating the moving velocity distribution of the tissue for each time phase by dividing this moving vector by the time difference between the frames of the two-dimensional image data.

The above arrangement can also achieve the same effects as those of the first embodiment.

(Third Embodiment)

The third embodiment of the present invention will be described next. An ultrasonic diagnosis apparatus 1 according to this embodiment measures a temporal change in the position of an ultrasonic probe 11 upon application of a dynamic load such as compression/release or a temporal change in pressure on the contact surface between the ultrasonic probe 11 and an object upon compression, and generates a reference waveform by using the measured change.

Figure 7:
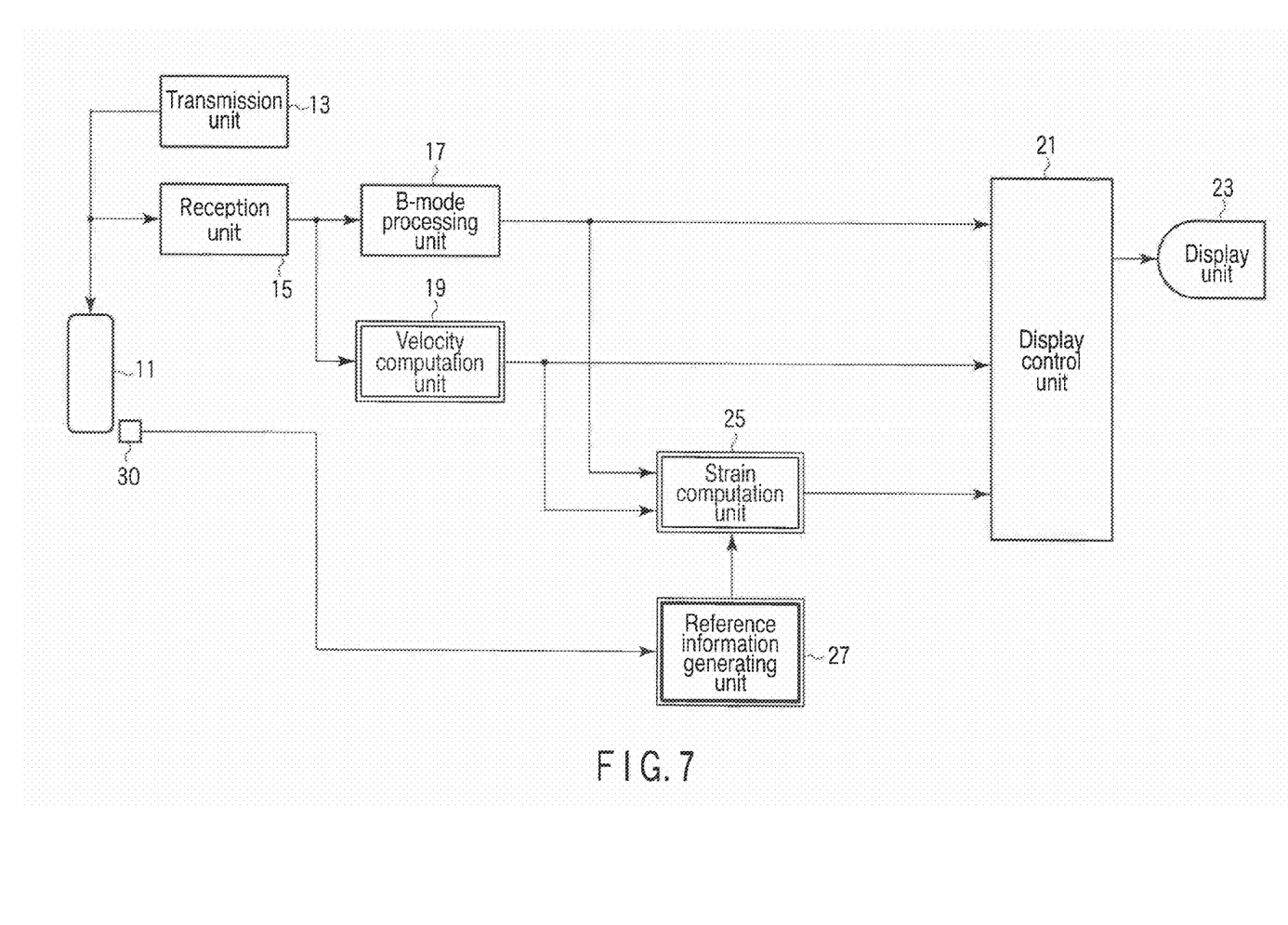
FIG. 7 is a block diagram showing the arrangement of an ultrasonic diagnosis apparatus 1 according to third embodiment.

FIG. 7 is a block diagram showing the arrangement of the ultrasonic diagnosis apparatus 1 according to this embodiment. As shown in FIG. 7, the ultrasonic diagnosis apparatus 1 further includes a sensor 30. The sensor 30 is a magnetic induction type position sensor which measures a temporal change in the position of the ultrasonic probe 11 upon application of a dynamic load such as compression/release or a pressure sensor which measures a temporal change in pressure on the contact surface between the ultrasonic probe 11 (or a compression attachment attached to the probe 11) and the object upon compression.

A reference information generating unit 27 receives the spatial position of the ultrasonic probe 11 or the pressure on the contact surface between the probe and the object in each time phase in a predetermined period, and plots it in time series. The reference information generating unit 27 then performs predetermined interpolation processing for the resultant data, as needed, to generate a reference waveform indicating a temporal change in average tissue velocity. In the reference waveform generated in this manner, a time phase in which the level of the ultrasonic probe 11 becomes maximal (or a time phase in which the pressure becomes 0 or minimal) corresponds to compression start time phase $t(V=0+)$, and a time phase in which the level of the ultrasonic probe 11 becomes minimal (or a time phase in which the pressure becomes maximal) corresponds to release start time phase $t(V=0-)$.

The above arrangement can also achieve the same effects as those of the first embodiment.

(Fourth Embodiment)

The fourth embodiment of the present invention will be described next. An ultrasonic diagnosis apparatus 1 according to this embodiment generates and displays a monitoring waveform (strain waveform) for indicating a deformed time phase on the basis of an average strain value for each frame itself which is obtained from a computed strain image.

Figure 8:
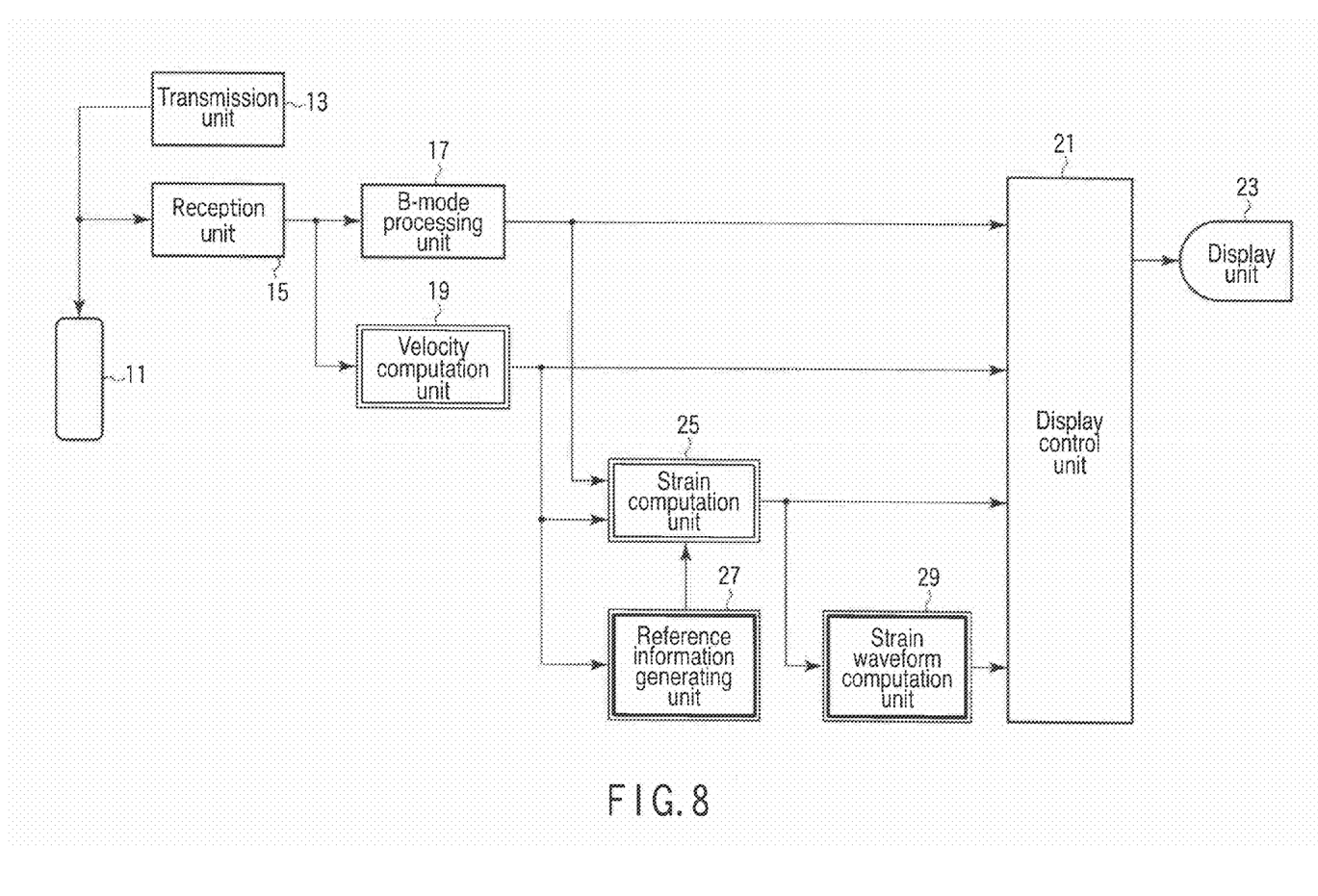
FIG. 8 is a block diagram for explaining the arrangement of an ultrasonic diagnosis apparatus 1 according to the fourth embodiment.

FIG. 8 is a block diagram for explaining the arrangement of the ultrasonic diagnosis apparatus 1 according to this embodiment. As shown in FIG. 8, the ultrasonic diagnosis apparatus 1 according to this embodiment further include a strain waveform computation unit 29.

The strain waveform computation unit 29 calculates an average strain value for each frame by using a strain image in each time phase in a predetermined period. Assume that the positive and negative directions are defined in the same manner as in the case of the generation of velocity information. The strain waveform computation unit 29 generates a strain waveform indicating a temporal change in average strain value by plotting, in time series, an average strain value for each frame in a predetermined period and performing predetermined interpolation processing for the resultant data, as needed. A display unit 23 displays the generated strain waveform instead of the monitoring waveform generated based on the average tissue velocity or together with the monitoring waveform generated based on the average tissue velocity.

According to this embodiment, a monitoring waveform (strain waveform) is generated by using an average strain value for each frame which is obtained from a computed strain image, and is displayed in the same form as that of an ECG waveform or the like in a scale corresponding to, for example, a compression strength. Therefore, displaying, in this manner, a monitoring waveform including waveforms corresponding to a plurality of number of times of compression/release in the past allows the probe operator to check whether stable compressing/releasing operation is performed. Based on such a monitoring waveform, freeze operation is performed in a time phase regarded as a time phase in which a strain image is properly and stably obtained in elastic imaging. This makes it possible to record the strain image as a diagnosis image. In elastic imaging, therefore, a proper strain image can be selected efficiently by using an objective reference. This can contribute to improvements in the quality of image diagnosis and in the efficiency of operation.

Note that the present invention is not limited to the above embodiments, and constituent elements can be variously modified and embodied at the execution stage within the spirit and scope of the invention. For example, the following are concrete modifications.

Each function associated with each embodiment can also be implemented by installing programs for executing the corresponding processing in a computer such as a workstation and mapping them in a memory. In this case, the programs which can cause the computer to execute the corresponding techniques can be distributed by being stored in recording media such as magnetic disks (floppy® disks, hard disks, and the like), optical disks (CD-ROMs, DVDs, and the like), and semiconductor memories.

Note that the above embodiments are not limited to real-time processing on an ultrasonic diagnosis apparatus, and can also be applied to a case in which after reception signals representing B-mode information and velocity information are stored, analysis is performed by reading stored data. In this case, although the monitoring effect introduced in the embodiments above is not provided, a deformed time phase can be automatically grasped and an optimal strain image synchronous with movement can be automatically obtained in the same manner as described above.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

The present invention described above can implement an ultrasonic diagnosis apparatus, an ultrasonic image processing apparatus, and a recording medium on which an ultrasonic image processing program is recorded, which can determine a time phase suitable for the start of strain computation in elastic imaging using TSI and can generate and display reference information as a suitable reference when applying a dynamic load on a tissue.

What is claimed is:

1. An ultrasonic diagnosis apparatus, comprising:
a computer implemented by processing circuitry configured to acquire ultrasonic image data corresponding to a plurality of time phases in a first period, including at least one contraction and one expansion, by ultrasonic scanning throughout the first period for an observation region of an object to be examined, the observation region repeating contracting motion and expanding motion upon application of a dynamic load including repetition of compression and release, generate velocity information concerning a tissue in the observation region in the plurality of time phases in the first period, generate reference information including a graphic chart of velocity of the observation region with time over a plurality of cycles, each of which includes the contracting motion and the expanding motion, determine a second period corresponding to at least one of the contraction motion and the expansion motion, in a period including at least part of the compression and the release, based on the reference information, execute time integration with respect to the velocity information in the second period to generate strain information concerning the tissue corresponding to a second plurality of time phases in the second period, and generate, based on the strain information, a strain image indicating a strain distribution of the observation region; and
a display configured to display the strain image in a predetermined form.

2. The ultrasonic diagnosis apparatus according to claim 1, wherein the computer is further configured to set, as a lower limit, a first time phase in which the velocity associated with the contracting motion or the expanding motion becomes 0, and to set, as an upper limit, the second plurality of time phases in the second period, and determine an integral interval for the second plurality of time phases.

3. The ultrasonic diagnosis apparatus according to claim 1, wherein the computer is further configured to determine, based on the reference information, a contracting period in which the observation region contracts due to the dynamic load including compression or a period in which the observation region expands due to the dynamic load including release, and to determine the second period in which the observation region contracts or in which the observation region expands.

4. The ultrasonic diagnosis apparatus according to claim 1, wherein the computer is further configured to acquire the ultrasonic image data by a tissue Doppler method, generate velocity information in the plurality of time phases in the first period based on the ultrasonic image data, and generate, based on the velocity information in the plurality of time phases in the first period, the reference information indicating changes in the contracting motion and the expanding motion with time.

5. The ultrasonic diagnosis apparatus according to claim 1, wherein the computer is further configured to acquire the ultrasonic image data in a B mode, generate velocity information in the plurality of time phases in the first period by executing pattern matching processing between two frames associated with a region of interest using the ultrasonic image data, and generate, based on the velocity information in the plurality of time phases in the first period, the reference information indicating changes in the contracting motion and expanding motion with time.

6. The ultrasonic diagnosis apparatus according to claim 1, wherein the computer is further configured to generate, based on a temporal change in a position of an ultrasonic probe used for acquisition of the ultrasonic image data, the reference information indicating changes in the contracting motion and expanding motion with time.

7. The ultrasonic diagnosis apparatus according to claim 1, wherein the computer is further configured to generate the reference information indicating changes in the contracting motion and the expanding motion with time based on a temporal change concerning a pressure on a contact surface between an ultrasonic probe used for acquisition of the ultrasonic image data and the object due to the dynamic load.

8. The ultrasonic diagnosis apparatus according to claim 1, wherein the display is configured to display the strain image while sequentially updating the strain image in a contracting period during which the observation region contracts, and to hold and display the strain image corresponding to a time phase at a time of an end of compression in a period during which the observation region expands.

9. The ultrasonic diagnosis apparatus according to claim 1, wherein the display is configured to display the strain image while sequentially updating the strain image in an expanding period during which the observation region expands, and to hold and display the strain image corresponding to a time phase at a time of an end of release in a contracting period during which the observation region contracts.

10. The ultrasonic diagnosis apparatus according to claim 1, wherein the display is configured to simultaneously display the strain image and a B-mode image associated with the observation region displayed like a moving image.

11. The ultrasonic diagnosis apparatus according to claim 1, wherein the display is configured to simultaneously display the reference information and the strain image.

12. The ultrasonic diagnosis apparatus according to claim 1, wherein the display is configured to display the reference information in a scale corresponding to a strength of the dynamic load.

13. The ultrasonic diagnosis apparatus according to claim 1, wherein the display is configured to display the reference information in a form including a plurality of compression periods and a plurality of release periods.

14. The ultrasonic diagnosis apparatus according to claim 1, wherein the computer is further configured to generate reference information indicating a change in strain concerning the tissue in the observation region with time by using the strain information, and the display is further configured to display the reference information indicating the change in the strain concerning the tissue in the observation region with time.

15. The ultrasonic diagnosis apparatus of claim 1, wherein the display is further configured to display the generated graphic chart of velocity.

16. An ultrasonic image processing apparatus, comprising:
   a memory configured to store ultrasonic image data corresponding to a plurality of time phases in a first period including at least one contraction and one expansion by ultrasonic scanning throughout the first period for an observation region of an object to be examined, the observation region repeating contracting motion and expanding motion upon application of a dynamic load including repetition of compression and release;
   a computer implemented by processing circuitry configured to generate velocity information concerning a tissue in the observation region in the plurality of time phases in the first period, generate reference information including a graphic chart of velocity of the observation region with time over a plurality of cycles, each of which includes the contracting motion and the expanding motion, determine a second period corresponding to at least one of the contraction motion and the expansion motion, in a period including at least part of the compression and the release, based on the reference information and to execute time integration with respect to the velocity information in the second period to generate strain information concerning the tissue corresponding to a second plurality of time phases in the second period, and generate, based on strain information, a strain image indicating a strain distribution of the observation region; and
   a display configured to display the strain image in a predetermined form.

17. A non-transitory computer readable medium which stores an ultrasonic image processing program which causes a computer to execute steps of:
   generating velocity information concerning a tissue in an observation region in a plurality of time phases in a first period including at least one contraction and one expansion by using ultrasonic image data corresponding to the plurality of time phases in the first period by ultrasonic scanning throughout the first period for the observation region of an object to be examined, the observation region repeating contracting motion and expanding motion upon application of a dynamic load including repetition of compression and release;
   generating reference information including a graphic chart of velocity of the observation region with time over a plurality of cycles, each of which includes the contracting motion and the expanding motion;
   determining a second period corresponding to at least one of the contraction motion and the expansion motion, in a period including at least part of the compression and the release, based on the reference information and executing time integration with respect to the velocity information in the second period to generate strain information concerning the tissue corresponding to a second plurality of time phases in the second period; and
   generating, based on strain information, a strain image indicating a strain distribution of the observation region.

* * * * *

UNITED STATES PATENT AND TRADEMARK OFFICE
CERTIFICATE OF CORRECTION

PATENT NO. : 9,451,930 B2  
APPLICATION NO. : 12/606249  
DATED : September 27, 2016  
INVENTOR(S) : Yasuhiko Abe

Page 1 of 1

It is certified that error appears in the above-identified patent and that said Letters Patent is hereby corrected as shown below:

On the Title Page

Item (63), the Related Application Data Information has been omitted. Item (63) should read:
-- Related U.S. Application Data
(63) Continuation of application No. PCT/JP09/053428, filed on Feb. 25, 2009 --

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*